US012207804B2

(12) United States Patent
Chaffringeon

(10) Patent No.: US 12,207,804 B2
(45) Date of Patent: Jan. 28, 2025

(54) COLLECTING DEVICE, KIT, MANUFACTURING PROCESS, SAMPLING METHODS AND USE

(71) Applicant: Bernard-Marie Chaffringeon, Pitesti (RO)

(72) Inventor: Bernard-Marie Chaffringeon, Pitesti (RO)

( * ) Notice: Subject to any disclaimer, the term of this patent is extended or adjusted under 35 U.S.C. 154(b) by 0 days.

(21) Appl. No.: 18/549,761

(22) PCT Filed: Mar. 9, 2021

(86) PCT No.: PCT/IB2021/051932
§ 371 (c)(1),
(2) Date: Sep. 8, 2023

(87) PCT Pub. No.: WO2022/189828
PCT Pub. Date: Sep. 15, 2022

(65) Prior Publication Data
US 2024/0041440 A1 Feb. 8, 2024

(51) Int. Cl.
*A61B 10/02* (2006.01)
*A61F 13/15* (2006.01)
*A61F 13/36* (2006.01)

(52) U.S. Cl.
CPC ........ *A61B 10/02* (2013.01); *A61F 13/15699* (2013.01); *A61F 13/15723* (2013.01);
(Continued)

(58) Field of Classification Search
None
See application file for complete search history.

(56) References Cited

U.S. PATENT DOCUMENTS 2,487,200 A    11/1949  Trager
4,515,167 A *   5/1985  Hochman .......... A61B 10/0012
                                                        607/70
(Continued)

FOREIGN PATENT DOCUMENTS

DE    202009016553 U    4/2010

*Primary Examiner* — Benjamin S Melhus
(74) *Attorney, Agent, or Firm* — Law Office of Andrei D Popovici, PC

(57) ABSTRACT

The present invention relates to a collecting device (1) for sampling at least one specimen from bodily cavities of humans and animals, comprising: —an elongated flattened pouch (20) having: an open end (200), a top side (201) opposed to the open end (200), situated at a proximal end (101) of the collecting device (1), and two lateral sides (202, 204); and—two creasing means (32, 34), each having a fixed end (301), which is fixed inside the pouch (20) at or in the vicinity of said top side (201) and a free end (303), which protrudes freely through said open end (200), configured such that upon pulling the free ends (303) of the two creasing means (32, 34) in opposite directions, the short side (201) of the pouch (20) is brought closer to the open end (200) while the pouch (20) adopts a creased shape (22). Preferably, the collecting device further comprises two sheets of fabric (40, 41), that are fastened to each other by fastening elements (25) such as welding lines situated at a distance of about 1 mm to 10 mm from proximal margins (401) of said sheets (40, 41) to form two proximal flaps (44, 46) fixed to each other by the fastening elements (25) such that the two flaps (44, 46) can transition form a closed state (47) to an open state (49). The present invention also relates to the use of the collecting device (1) for sampling of at least one specimen from bodily cavities of humans and animals, to a kit and methods for sampling and to a process for producing the collecting device (1).

19 Claims, 5 Drawing Sheets

(52) U.S. Cl.
CPC ........ *A61F 13/15747* (2013.01); *A61F 13/36* (2013.01); *A61F 2013/15869* (2013.01)

(56) References Cited

U.S. PATENT DOCUMENTS

| | | | |
|---|---|---|---|
| 4,743,237 A * | 5/1988 | Sweere | A61F 13/2051 |
| | | | 604/904 |
| 4,775,377 A * | 10/1988 | Sweere | A61F 13/2085 |
| | | | 53/134.2 |
| 5,659,934 A * | 8/1997 | Jessup | A61F 13/26 |
| | | | 604/385.18 |
| 5,688,260 A | 11/1997 | Blanton | |
| 5,795,346 A * | 8/1998 | Achter | A61F 13/2051 |
| | | | 604/385.18 |
| 5,807,372 A * | 9/1998 | Balzar | A61F 13/34 |
| | | | 600/575 |
| 5,873,971 A * | 2/1999 | Balzar | A61F 13/2085 |
| | | | 156/227 |
| 6,142,928 A * | 11/2000 | Zunker | A61F 2/005 |
| | | | 600/29 |
| 2013/0184684 A1* | 7/2013 | Yardley | A61F 13/126 |
| | | | 606/162 |
| 2015/0005667 A1* | 1/2015 | Zavala | A61F 13/34 |
| | | | 600/575 |
| 2016/0120708 A1 | 5/2016 | Chaffringeon | |
| 2016/0273059 A1* | 9/2016 | Benshaul | C12Q 1/708 |
| 2017/0112478 A1* | 4/2017 | Ryu | A61B 10/0291 |
| 2018/0344300 A1* | 12/2018 | Burrows | A61B 10/0291 |
| 2018/0353737 A1 | 12/2018 | Chaffringeon | |
| 2020/0188189 A1* | 6/2020 | Strong | B65H 20/00 |
| 2020/0390425 A1 | 12/2020 | Chaffringeon | |
| 2022/0192642 A1* | 6/2022 | Hooi | A61B 10/0045 |

* cited by examiner

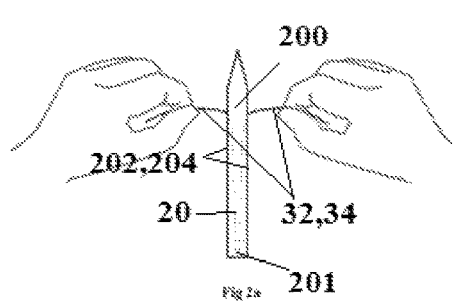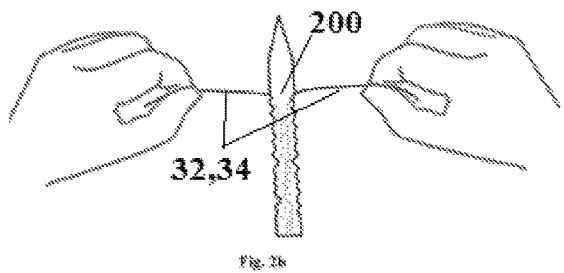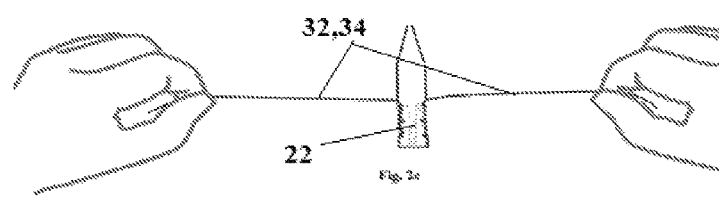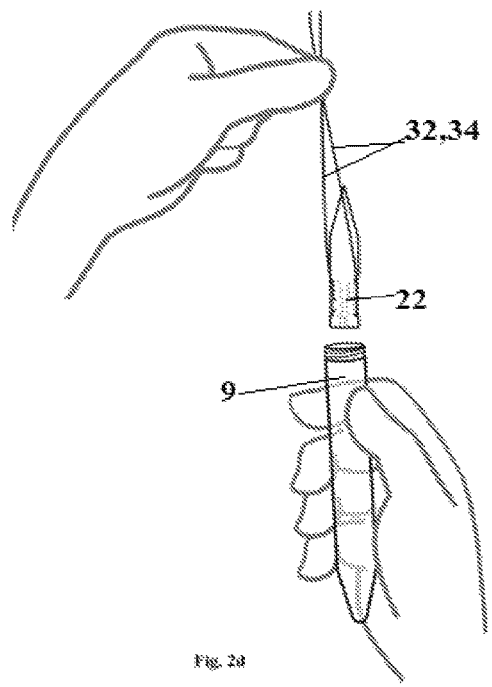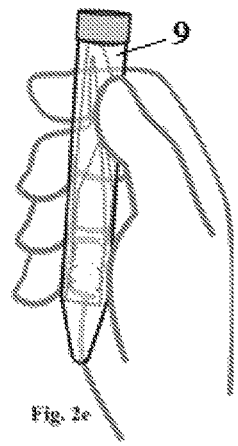

COLLECTING DEVICE, KIT, MANUFACTURING PROCESS, SAMPLING METHODS AND USE

The present invention relates to the field of sampling for specimens such as cells, cell residues, proteins, DNA, RNA, and/or other material from bodily cavities such as the vaginal cavity, rectal cavity, oral or nasal cavity.

BACKGROUND

Collecting specimens such as cytological, DNA, RNA, viruses such as the Coronavirus or HPV, and/or biologic samples for testing, study and diagnosis, especially for cervical cancer or STIs usually requires a complex examination and an often painful sampling made by a trained specialist (physician or nurse). Such samplings for testing for cervical cancers or STIs are traditionally performed on women by a gynecologist by inserting a speculum into the patient's vagina in a manner to expose the cervix of the uterus and then inserting a cervical scraper (with a swab or a brush) for sampling tissue from the endocervical canal and cervical os. The cervical scrapers are designed to scratch the tissue in order to take samples of tissue. Throughout this process, the woman must remain in a reclining (gynecological) position. Finally, the obtained specimen is applied directly on a glass slide, or placed into a recipient containing a liquid preservative in order to go through the analysis and evaluation steps. However, in about 30% of cases, unsatisfactory specimens are collected by this technique, leading to the need to repeat the procedure or to false or incomplete results. Recently, self-sampling devices, methods and kits have been developed, which allow the user to collect specimens in private and/or following a less traumatic procedure.

WO2019/106408 discloses a self-sampling kit comprising a sampling cloth designed to be inserted into the bodily cavity and a sealable recipient for storing and transporting said sampling cloth to laboratory and an applicator for inserting the sampling cloth into the bodily cavity. The sampling cloth disclosed is suitable for collecting specimens, being flexible, atraumatic, and having an absorbency of less than 3.5 g/g measured using the Syngina protocol for measuring the absorbency of tampons, and a low thickness and is thermo-fusible. The sampling cloths in this document are made from one sheet of fabric, which may be folded to form a pocket for the insertion of the applicator. After removal, the sampling cloth is inserted into a recipient that is sealed and sent to a diagnostic facility. The document requires that "At least one of the openings of said recipient has dimensions sufficient to allow the user of the kit to easily place the sampling cloth inside the recipient, preferably without squeezing the cloth, which might result in removing part of the collected specimens. Therefore, the dimensions of said opening will depend on the width of the sampling cloth.". Indeed, attempting to insert the soft, flexible cloth into a recipient without losing part of the harvested specimens can be difficult and necessitates that the sealable recipient be quite large, which would also mean that a correspondingly large volume of preserving liquid would have to be provided therein, thus the entire kit can become big, heavy and expensive. This is a serious drawback especially in developing countries.

The aim of the present invention is to provide an inexpensive sampling cloth, sampling kit and method, with improved precision rate and efficacy in sampling, self-sampling, and preserving specimens like cells, cell residues, DNA, RNA, proteins, viruses, bacteria, parasites, or fungi and/or other materials of interests from the bodily cavities of humans and animals.

This aim is achieved by a collecting device according to the invention. In another aspect, the present invention refers to a kit comprising the collecting device of the invention together with a suitable recipient and applicator. In another aspect, the present invention refers to the use of said collecting device for sampling at least one specimen from bodily cavities of humans and animals, to a process for manufacturing the collecting device and to methods for self-sampling and diagnostic.

Definitions

By sampling it is meant a process of harvesting specimens wherein the sampling procedure can be performed by a professional, such as a doctor or a nurse, by an individual on him- or herself, or by an individual on another individual or animal, without the assistance from a trained professional.

By specimen it is meant any cell, cell residue, DNA, RNA, protein, virus, bacterium, parasite, fungus and/or other material of interests.

The collecting device according to the present invention is designed to be inserted into a bodily cavity of a human or animal, by means of an applicator. Thus, a direction of insertion is defined, which is an axis crossing the collecting device and being oriented from the end of the collecting device that remains outside the cavity, called distal end of the collecting device, to the end of the collecting device that first contacts said cavity, called proximal end of the collecting device. When looking in the direction of insertion, the top of the collecting device or the upper part is represented by the extremity of the collecting device that comprises its proximal point; that is the point that first contacts the cavity. At the same time, the bottom of the collecting device or the lower part is represented by the extremity of the collecting device that comprises its distal end; that is the point of the collecting device opposite to the proximal point, i.e. placed at the furthest distance from the proximal point on the insertion direction. In some embodiments, part of the collecting device protrudes outside from the vaginal or rectal cavity. In such a situation, the bottom of the collecting device will also comprise such part of the collecting device. Taking into account the above definitions, then lateral sides of the collecting device will be the left and right extremities, considering the top and bottom as defined above.

According to the invention, "upper", "up" or "above" will refer to a first point or part situated closer to the top of the collecting device relative to a second point of reference, while the second point will be situated "lower", "down" or "below", respectively, to said first point or part.

According to the invention, "oriented upwards" means oriented towards the top of the collecting device, while "oriented downwards" means oriented towards the bottom of the collecting device. By "moving forward" it is to be understood according the invention movement in the direction of insertion of the collecting device into said cavity.

Disclosure

Collecting Device

One aspect of the present invention refers to a collecting device for sampling at least one specimen from bodily cavities of humans and animals, having a proximal end which is the end of the device to first contact said bodily cavity during use and a distal end opposed to said proximal end, comprising:
- an elongated flattened pouch having: an open end, a short side, also called top side, opposed to the open end, situated toward or at the proximal end of the collecting device, and two long sides, also called lateral sides, preferably having a length longer than the length of the short side; and
- two creasing means, each having a fixed end, which is fixed inside the pouch at or in the vicinity of said short side, and a free end, which protrudes freely through said open end, wherein the collecting device is configured such that upon pulling the free ends of the two creasing means in opposite directions each substantially perpendicular to one of the two long sides, the short side of the pouch is brought closer to the open end while the pouch adopts a creased shape.

In a preferred embodiment of the invention, the collecting device comprises at least one further segment integrally formed with the fabric of the pouch, extending from the open end of the pouch towards the distal end of the collecting device, having dimensions such that, after the collecting device is inserted into the bodily cavity, said at least one further segment protrudes outside said bodily cavity and can be used for the removal of the collecting device from the bodily cavity.

A further aspect of this invention refers to the use of the collecting device for the sampling of at least one specimen from bodily cavities of humans and animals.

Material

The mentioned elongated flattened pouch of the invention is made of a material suitable to be introduced into a bodily cavity such as the vagina or rectum. Thus, the pouch can be comfortably fitted inside the bodily cavity.

Said suitable material will be flexible, by which it is to be understood a material that will bend and unbend to follow the shape of the bodily cavity. Also, a suitable material will be preferably atraumatic, by which it is to be understood a material that may be put into contact with or made to slide over or wipe a surface of a body membrane such as the vaginal or rectal mucosa without causing any injury or discomfort such as irritation, pain etc., preferably a fabric with a soft carded smooth surface. The use of a pouch made of such a flexible, atraumatic material has the advantage that avoids the irritation of the bodily cavity, pain and discomfort during the insertion. Thus, when the pouch is introduced into the bodily cavity with the aid of an applicator, the fabric of the pouch above and around said applicator will protect the vaginal mucosa from direct contact with the hard material of the applicator.

Advantageously, as mentioned in document WO2019/106408, a suitable material for the pouch is a material that can catch specimens from the bodily cavity and preferably retain said specimens on its surface, while at the same time being able to subsequently easily release said specimens so that they can be analyzed. Therefore, the pouch has advantageously a surface coming into contact with the bodily cavity, but little or no absorbency, so that only a small amount of the specimens are absorbed into the fabric of the pouch, most remaining attached to its surface. To this aim, the absorbency should be preferably less than 3.5 g/g, more preferably less than 3 g/g, most preferably less than 2 g/g measured using the Syngina protocol for measuring the absorbency of tampons. For example, an absorbency of 3.5 g/g means that 3.5 grams of liquid are absorbed per 1 gram of material. Preferably, the pouch is made of a fabric having low thickness. A pouch having low thickness will be able to catch the specimens on its surface, but it will not, or only minimally, transfer, collect and retain them in its depth. Such a pouch has the advantage that, unlike a sponge or a tampon, it will not retain inside the collected specimens (cells, proteins, DNA, etc.) during the analysis and evaluation steps. Instead, the pouch will easily liberate the specimens from the pouch, so the final quantity of specimens to be analyzed is maximized, which raises the precision rate (accuracy) of the sampling test. The thickness of the pouch should be of 3 mm or less, preferably 2 mm or less, more preferably 1 mm or less, even more preferably 0.6 mm or less, which means a thickness much smaller compared to a normal tampon. Advantageously, the material of the pouch has a basis-weight of approximately 60 g/m$^2$ to 70 g/m$^2$.

Various materials having the above characteristics, suitable for sampling inside a bodily cavity are known to the specialists. An illustrative list of such materials can be found in WO2019/106408, the disclosure of which is herewith incorporated in its entirety by the present reference. Namely, the material of the pouch, suitable to be comfortably inserted into a bodily cavity, may be chosen from the group of a woven or non-woven textile, for example made of synthetic fibers (such as polyester, polypropylene, polyethylene, polyamide, polyacetate, polyvinyl acetate), semi-synthetic fibers (such as viscose, modal, lyocell), plant fibers (such as cotton), animal fibers (such as silk), or combinations thereof. In a preferred embodiment, the material is biodegradable, thus reducing the impact on the environment. Preferably, the material is a non-woven textile made of synthetic fibers, since such materials are atraumatic and have the desired low absorbency. Also, such products may have low production costs. In a preferred embodiment, the material is also thermo-fusible, so that it may be welded. In a more preferred embodiment, the pouch is made of a non woven fabric with a soft carded smooth surface comprising a non-woven polyethylene/polyester bicomponent.

Preferably, such fabric has the following properties:
- average basis weight (mass per unit area), measured with WSP 130.1 Test method, of around 59.20 g/m$^2$,
- average tensile strength MD, representing the force per unit width which is required to rupture a sample orientated in the machine direction, measured with a Test method following WSP 110.4 using a sample width of 25.4 mm (1 inch), a clamp distance of 127 mm (5 inch) and a speed of 500 mm/min (19.7 inch/min), of around 48.86 N/inch
- average elongation at F-max MD, representing the relative increase in length at the maximum force applied on a sample orientated in the machine direction, measured with a Test method following WSP 110.4 using a sample width of 25.4 mm (1 inch), a clamp distance of 127 mm (5 inch) and a speed of 500 mm/min (19.7 inch/min), of around 38.40%.

Dimensions

The collecting device according to the invention is suitable to be inserted into a bodily cavity such as the vaginal, rectal, oral, nasal cavity of a human or animal. Thus, the person skilled in the art will understand to choose its dimensions adapted to the dimensions of the bodily cavity where it is to be inserted.

For example, the vagina and rectum are open cavities in the form of fibro-muscular tubes with walls that are easily distensible. The vagina is in the form of a tube having at the extremities an external opening (the vaginal opening) and an internal opening (communicating with the uterus). The rectum is in the form of a tube having at the extremities an external opening (the anus) and an internal opening (communicating with the large intestine); near the external opening it has a dilated portion, the rectal ampulla, where the pouch according to the invention is meant to be housed. The external openings of the vagina and rectum are substantially circular. The width (diameter) of the tubes (vagina and rectum) varies throughout their length, with the minimum width being at the external opening of the bodily cavity. For example, the human adult vagina or rectum at rest have, at the external opening, a width of about 2.5 cm.

Whatever the shape of the collecting device when outside the bodily cavity, due to the fact that it is made of a flexible fabric, when inserted into the bodily cavity by pushing it through the substantially circular external opening, it will collapse, e.g. deform, fold, strangle and/or twist to pass through the external opening and then will unfold to roughly follow the shape of the cavity. Therefore, the dimensions of the collecting device for inserting into the human vaginal or rectal cavities will be chosen such that, in said collapsed position, the maximum width of the collecting device will be of less than 2.5 cm, so that it can be comfortably inserted into the bodily cavity. In preferred embodiments, the width of the collecting device for vaginal sampling may be chosen, for example, to be between 1 cm and 4 cm, preferably from 1 cm to 3 cm, most preferably from 1 cm to 2 cm such as 1.2 to 1.5 cm. Such dimensions would be sufficient to collect samples from the entire inner surface of the vagina, while maintaining at the same time the dimensions of the collecting device sufficiently low to be more comfortable to insert and keep inside the bodily cavity and also less expensive to produce and able to fit into a similarly less expensive recipient with smaller dimension.

When inserted into the bodily cavity, which means after the collecting device has been pushed inside the bodily cavity, it will preferably take a position having the proximal end closest to the internal opening of the bodily cavity. The distance from the proximal end to the distal end of the collecting device defines the length of the collecting device. Thus, the skilled person will be able to shape/choose the dimensions of the collecting device depending on the expected dimensions of the bodily cavity to be sampled.

For example, depending for example on the age, ethnic group or medical history of the intended recipient, a collecting device for vaginal sampling may have a length of about 8 to 16 cm, preferably of about 10 to 14 cm, such as about 12 to 13 cm.

Creasing Means

By creased state is meant a state wherein the pouch assumes a contracted, folded, usually accordion-like shape, such that the short side of the pouch is brought closer to its open end than when the pouch is in extended, un-creased shape.

Each of said creasing means is preferably in the form of a thread, string, strip or ribbon.

Each of said creasing means has a fixed end, which is fixed inside the pouch at or in the vicinity of the short side of the pouch, and a free end which protrudes freely through the open end of the pouch. The length of the creasing means is adapted such that their distal, free ends protrude enough out of the open end of the pouch to be possible to grip each of them using the hand, such as for example between two fingers, and pull them in order to crease the pouch. For example, the free, distal ends protrude for at least 10 mm from the pouch.

As mentioned, each of the creasing means has a fixed end, which is fixed inside the pouch at at least one fixing point placed at or in the vicinity of the short side of the pouch. The creasing means may be attached to the pouch in any suitable way known in the art that would allow a good fixation, without detaching from the pouch during use, such as by welding, sewing, pasting, stapling, buttoning, knotting or gluing. In a preferred embodiment, the short side of the pouch is represented by a welding area that also welds the ends of the creasing means to the pouch. Preferably, said welded area is made up by at least two welding rows, each made of welding spots and/or welding lines.

By gripping the free ends of the two creasing means and pulling them in opposite directions each substantially perpendicular to one of the two long sides of the pouch, the short side of the pouch is brought closer to the open end while the pouch adopts a creased shape. When pulled, the two creasing means apply pressure on the two long sides at contact zones, also called articulation points, at the distal extremities of said long sides. These contact zones act as bending points for the creasing means. By pulling the creasing means, they apply pressure on the long sides of the pouch at the bending points, and at the same time pulling on their fixing points at the short side of the pouch. This causes the long sides of the pouch to slide along the creasing means at the bending points towards the short side of the pouch, and forces them to adopt a creased shape. As a result, the entire pouch adopts a creased shape, that has significantly smaller dimensions that its extended shape. For example, in one embodiment, a collecting device with the pouch in extended shape having the length of 12 cm, gets to a length of about 4.5 cm in creased shape.

Reducing the dimensions of the pouch by making it assume a creased shape has the advantage that the collecting device can be housed in a smaller recipient for transporting to a testing facility. Moreover, the pouch in creased shape has significantly greater rigidity than in extended shape. This makes it easier to manipulate and to introduce into a recipient, further allowing for a smaller recipient to be used, which uses less raw material and is less expensive to produce. When the collecting device is introduced into the recipient with the pouch first, meaning that the pouch in the creased state is the first part of the device to enter the recipient, the fact that the pouch is made rigid by the creased state makes is much easier to introduce. The user can for example easily introduce the collecting device pouch-first, holding the device by the distal ends of the creasing means, thus avoiding the risk of contamination by touching the pouch. Also, the sealable recipients for housing and transporting the collecting device to a laboratory often contain means for preserving or preparing the sampled specimens, such as distilled water, saline water, or culture medium, or such means are added into the recipients at the testing laboratory. Since the pouch, which represents the main sampling part of the collecting device, has reduced dimensions, it can be fully submerged in a smaller volume of said preserving means.

The creasing means may be made of any material which does not tear when a force necessary to crease the pouch into the creased shape is applied thereon. Preferably, rupture resistance of such means is above 50 N, such as a cotton yarn having a metric yarns number Nm of 16/4.

In preferred embodiments, said creasing means are made of an elastic material, which ensures that the pouch maintains the creased shape for a longer time. After the user stops pulling the creasing means, the creased pouch tends to slowly revert to a less compacted shape. If the creasing means are made of elastic material, when released, they elastically contract in order revert to a shorter size. While contracting, the elastic material of the creasing means catches and fixes creases of the pouch, and thus does not allow the pouch to revert to a less compacted shape. This gives the user more time to transfer the collecting device into the recipient without the pouch losing its compacted, small dimensions, and ensures that the pouch keeps the creased state after insertion into the recipient, so it can remain fully submerged in a small volume of preserving liquid.

In one embodiment, the collecting device has dimensions such that only the creasing means protrude from the bodily cavity during sampling. In this embodiment, said creasing means are also used as means for removal from the bodily cavity.

In other embodiments, the collecting device has dimensions such that part of the pouch protrudes outside the bodily cavity during sampling. This protruding, distal end of the pouch can be used as means for removal of the pouch from the bodily cavity, by itself or together with the creasing means protruding therefrom.

In yet other, preferred embodiments, the collecting device has at least one further segment, for example made of the same fabric as the pouch, extending from the open end of the pouch towards the distal end of the collecting device. Said further segment(s) remain(s) outside the bodily cavity during sampling, and can be used as means of removal of the collecting device from the bodily cavity. Preferably, the creasing means of this embodiment have a length such that their free ends do not surpass the distal extremity of said further segment(s). This embodiment has the advantage that it ensures that the user uses said further segments as means for removal of the collecting device. The creasing means do not protrude beyond the further segment(s) and are not used as removal means, or they are gripped only together with the further segments. This avoids the possibility that, by pulling the creasing means in order to remove the collecting device, the poach turns inside out during removal, and thus the collected specimens get inside the pouch and become more difficult to release. At the same time, in this embodiment the further segments protruding from the bodily cavity are more comfortable for the user than if the pouch protrudes.

Further Segment(s)

In some embodiments, the collecting device of the invention further comprises at least one further segment, for example made of the same piece(s) of fabric as the pouch, extending from the open end of the pouch towards the distal end of the collecting device Said further segment(s) protrude(s) outside the bodily cavity during sampling, such that it/they can be used as means for removal of the pouch from the bodily cavity. Preferably, each of said at least one further segment is made of a sheet of flat fabric, by which it is meant a single sheet of fabric that is in a substantially bi-dimensional shape, i.e. is not folded nor fastened to other sheet. More preferably, at least one the further segment(s) has a V-shape, meaning that it narrows down from the open end of the pouch toward the distal end of the collecting device. Such a V-shape has the advantage that it makes it easier to see and grip the free ends of the creasing means. Also, for example for a vaginal or rectal collecting device, such a V-shape is more comfortable for the user to wear for a longer time outside the bodily cavity during sampling, while the pouch is inserted inside the cavity.

In a preferred embodiment, the collecting device has two further segments, both having the mentioned V-shape.

Two Sheets

In some embodiments, the collecting device comprises two sheets of fabric, each having a proximal margin situated at the proximal end of the device, a distal margin situated at the distal end of the device, and two lateral margins. Embodiments wherein the collecting device comprises two sheets of fabric are preferred because the method of producing the device from two sheets of fabric is simple and fast, as it will be further explained.

Fastening Elements

Said sheets of fabric are fastened to each other by fastening elements such as continuous welding lines, spot welding rows, sewing lines, and/or glue lines, which form the short side and the two long sides of the pouch.

Angle of Welding Spots

In preferred embodiments, the fastening elements forming each of the two long sides of the pouch are single straight rows of welding spots having substantially elongated shapes. Such elongated welding spots have a long axis, a proximal end and a distal end. In preferred embodiments, the elongated welding spots are placed in the corresponding rows such that said long axes of the welding spot form a similar angle to the direction of their corresponding row. In a preferred configuration, the mentioned similar angle is an acute angle formed by the long axes of the welding spots to the direction of the corresponding long side toward the proximal end of the collecting device. Therefore, the proximal end of each welding spot is at the same time closer to the short side of the pouch and to a longitudinal central axis of the pouch. This arrangement has the effect that, when pulling on the creasing means, the angled welding spots lead the pouch to fold into small, even, regular, symmetric creases, thus adopting a compact creased shape that is easier to introduce into a recipient.

Short Side Two or More Rows

In preferred embodiments, the fastening elements forming the short side of the pouch are made of two or more rows of welding spots and/or lines of continuous welding. For example, said short side of the pouch may be made of two rows of welding spots and a line of continuous welding between the two rows. A fastening element at the short side made of two or more rows and/or lines of welding is more resistant to the force of pushing of the applicator. Moreover, this is also advantageous for the embodiments wherein the two creasing means are fixed inside the pouch by the fastening elements forming the short side of the pouch. The multiple welding rows and/or lines ensure a sturdier, more secure fixation of the creasing means.

Rectangular

In one embodiment, said two long sides of the pouch are parallel to each other and perpendicular to said short side. Thus, the fastening elements form a contour in the shape of three sides of the rectangle, wherein the short side of the rectangle forms the short end of the pouch, and the long sides of the rectangle form the long sides of the pouch. In preferred embodiments, said long sides of the pouch are situated at or in the vicinity of the lateral margins of the sheets.

Further Segments

In preferred embodiments, each sheet of fabric has a segment that is fastened to the other sheet to form the pouch and at least one of said sheets of fabric has a further segment at the distal margin that is not fastened. Said further segment(s) can remain outside the bodily cavity and be used as means of removal of the collecting device from the bodily cavity. Preferably, at least one the further segment(s) narrows down from the open end of the pouch toward the distal end of the collecting device, which makes it easier for the user to see and grip the free ends of the creasing means. Also, for example for a vaginal or rectal collecting device, such a narrowing shape is more comfortable for the user to wear for a longer time outside the bodily cavity during sampling. In a preferred embodiment, both sheets have further segments having the mentioned narrowing shape, such as a V-shape.

Also, in preferred embodiments, the free end of each of said creasing means can reach out distally of the pouch to a point that is at least 10 mm beyond said open end of the pouch but not beyond the distal margin of the longer of said further segments. This arrangement will prevent the user from using the creasing means as the only means for removal the collecting device from the bodily cavity, so the pouch is not turned inside out during removal.

Flaps

An alternative collecting device may comprise two sheets of fabric, each having a proximal margin situated toward a proximal end of the device, and a distal margin situated toward a distal end of the device, wherein said sheets are fastened to each other by a fastening element such as a continuous welding line, spot welding row, sewing line, and/or glue line situated at a distance of about 1 mm to 10 mm, such as 1 to 3 mm, 1 to 5 mm, 1 to 8 mm from the proximal margins of said sheets. Preferably, the collecting device comprises two sheets of fabric, each having a proximal margin situated at a proximal end of the device, a distal margin situated at a distal end of the device, wherein said sheets are fastened to each other by fastening elements such as continuous welding lines, spot welding lines, sewing lines, and/or glue lines to form a pouch having:

an open end,
a short side opposed to the open end and situated toward the proximal end of the collecting device, and
two lateral sides, wherein said short side of the pouch is situated at a distance of about 1 mm to 10 mm, such as 1 to 3 mm, 1 to 5 mm, 1 to 8 mm from the proximal margins of said sheets. Because said fastening element is situated at a distance such as 1 to 10 mm from the proximal margins of the two sheets, the two sheets of fabric form, toward the proximal end of the collecting device, two proximal flaps, representing the sections of said two sheets extending from the fastening element, such as the short side of the pouch, to the proximal margins of each sheet. The two flaps can be symmetrical, meaning that they have similar shapes and dimensions, or asymmetrical, meaning they can have shapes and dimensions different from each other. As mentioned, said two proximal flaps are fixed to each other by the fastening elements along the short side of the pouch, and have each a free margin opposite the short side of the pouch that is also the proximal margin of the respective sheet of fabric. The two proximal flaps can transition from a closed state, wherein their two free margins touch or are very close to each other, to an open state, wherein their two free margins get away from each other. Said proximal flaps each has an inner face, which is the surface of the flap positioned toward the other flap when in closed state, and an opposite outer face, which is the surface of the flaps positioned toward the exterior of the device when in closed state. A collecting device provided with such proximal flaps can more efficiently sample specimens, because, during insertion of the collecting device into the bodily cavity, the proximal flaps transition to said open state, by the friction with the walls of the bodily cavity. This allows the specimens to be collected mainly on the inner faces, which are often positioned in the bodily cavity, when the collecting device is fully inserted, at the most important area for sampling, which is usually in the vicinity of the internal opening of the bodily cavity. During removal from the bodily cavity, the proximal flaps transition back to the closed state, thus catching the specimens between the flaps, on their inner faces. This ensures that a sufficient amount of specimens are successfully sampled and kept on the inner faces of the flaps, which are not lost because only the external faces and rest of the collecting device are wiped due to friction with the walls of the bodily cavity during removal.

In preferred embodiments, the flaps as described above are provided together with any collecting device of the present invention Preferred Embodiment In a preferred embodiment, the collecting device comprises:

two sheets of fabric each comprising a first segment that is inserted into the bodily cavity when sampling, wherein the two first segments have substantially similar rectangular shapes, with the long sides of the rectangles forming lateral margins of the collecting device, and one of the short sides of the rectangles forming proximal margins that are placed at the proximal end of the collecting device, the two rectangular first segments being positioned such that they totally cover each other, and are fastened to each other by fastening elements such as spot welding rows and/or continuous welding lines, forming an elongated flattened pouch, wherein said elongated flattened pouch has:

an open end that may continue with a further segment,
a short side opposed to the open end, situated at a distance of about 1 mm to 10 mm from said proximal margins of the sheets of fabric, and
two long sides placed at or in the vicinity of said lateral margins and running along the length of the lateral margins up to the open end;

at least one of the sheets comprising a further segment that remains at least partially outside the bodily cavity during use, for gripping and removing the device from the bodily cavity, said further segments not being fastened to each other, one or both of said further segments preferably having a distal termination that narrows down toward the distal end of the collecting device.

and two creasing means such as threads or elastic threads, each having a fixed end, which is fixed inside the pouch at or in the vicinity of said short side, and a free end, which protrudes freely out of the pouch through said open end, but does not go beyond the distal termination of said further segments, wherein the collecting device is configured such that upon pulling the free ends of the two creasing means in opposite directions substantially perpendicular to the long sides, the short side of the pouch is brought closer to the open end while the pouch adopts a creased shape.

The collecting device of the present embodiment has the advantages:

it can be produced by a simple, continuous process, by running at the same time into a machine two sheets of fabric and two creasing means between them to form a continuous sandwich-like structure, and at regular intervals cutting out into the desired final shape the two sheets of fabric and the two creasing means, and simultaneously fastening the two sheets together by welding, thus forming the pouch and fixing the two creasing means, the fact that the short side of the pouch is situated at a distance of about 1 mm to 10 mm from said proximal margins of the sheets of fabric, has the effect that the two sheets form, toward the proximal end of the collecting device, two proximal flaps, representing the sections of said two sheets extending from the short side of the pouch to the proximal margins of each sheet. As mentioned above, a collecting device provided with such proximal flaps can more efficiently sample specimens, because, during insertion of the collecting device into the bodily cavity, the proximal flaps transition to an open state, allowing the specimens to be collected on their inner faces, and, during removal from the bodily cavity, the proximal flaps transition back to a closed state, thus catching the specimens between the flaps. This ensures that a sufficient amount of specimens are successfully sampled and kept on the inner faces of the flaps, which are not lost due to the friction of the collecting device with the walls of the bodily cavity during removal;

the collecting device is provided with further segment(s) that can remain outside the bodily cavity and be used as means of removal of the collecting device from the bodily cavity. At least one and preferably both further segment(s) narrow(s) down from the open end of the pouch toward the distal end of the collecting device into a V-like shape, which makes it easier for the user to see and grip the free ends of the creasing means, and is more comfortable for the user to wear for a longer time outside the bodily cavity during sampling. In a preferred embodiment, both sheets have further segments that are similar, for example being cut out simultaneously as in the process mentioned above. Also, the fact that the free ends of said creasing means do not go beyond the distal termination of said further segments prevents the user from using the creasing means as the only means for removal the collecting device from the bodily cavity, so the pouch is not turned inside out during removal.

Kit

In another aspect of the present invention it is disclosed a sampling kit, comprising a collecting device as described above, an applicator for inserting into the pouch to introduce at least part of said collecting device inside a bodily cavity, and a sealable recipient for receiving the collecting device after sampling.

The sampling kit may further comprise labeling means, such as a label for writing the data of the patient from whom the sample was taken and/or instructions for using the sampling kit.

Applicator

The collecting device according to the invention may be inserted into the bodily cavity by using an applicator such as a pushing tool. The pushing tool or applicator will have a shape, and dimensions adapted to those of the bodily cavity for which it is intended and the strength necessary to be able to push the collecting device inside the bodily cavity. The applicator may be disposable (one use-only) or reusable. The applicator may be made of any suitable material, such as plastic, silicon, wood, metal (such as stainless steel, titanium, or gold plated), cardboard etc. Preferably, the applicator is made of low density polyethylene PE-LD, which has low production costs, good flexibility, low weight and can be cleaned and reused.

The applicator may be releasably inserted, inside the pouch of the collecting device. Preferably, the width of said pouch is 1-6 mm bigger than the diameter of the applicator, for a smooth insertion and removal. Optionally, the applicator may have a gripping area, for gripping during insertion of the sampling cloth and during removal of the applicator from the bodily cavity. Said gripping area may have an adherent surface, or may be shaped so that it can be easily and firmly held by the human hand. For example, the applicator may have, along the gripping area, a series of recesses or elevations.

For instance, the applicator may be made in the form of a tubular body, having a proximal end (head), which is the end that first enters the bodily cavity and a distal end, which is the end remaining outside the bodily cavity and being optionally provided with gripping means. For use for a human vaginal collecting device, such an applicator may have a length (the height of the tube) of about 120 mm and a width (diameter of the tube) of about 8 to 12 mm, such as 10 to 11 mm.

Sealable Recipient

The recipient of the sampling kit is made of a suitable standard material such as plastic, and is preferably a standardized recipient that is easily accessible and mass produced, such as a plastic tube provided with a thread cap. The recipient has the dimensions adapted to house the collecting device of the invention. Preferably, the dimensions of the recipient are adapted to house the collecting device when in creased shape. That is to say, a recipient may be used for the kit of the invention that has reduced dimensions such that the collecting device can be introduced with its pouch in creased shape, but the collecting device with the pouch in extended shape could not be introduced therein, or could be introduced with difficulty, thus jeopardizing the amount of sampled specimens and/or contaminating the collecting device. This has the effect that a smaller than usual dimension of the recipient can be used, which is less expensive and needs less volume of preserving liquid.

The recipient is provided with at least one opening having dimensions sufficient to allow the user of the kit to insert the collecting device with the pouch in its creased shape inside the recipient.

The recipient is sealable, by which it is meant that any opening of said recipient is provided with sealing means, ensuring that it can be securely sealed after inserting the collecting device, to ensure its content cannot drain out and/or be contaminated.

Optionally, said recipient may contain means for preserving the specimen or further preparing it for a desired subsequent examination, such as distilled water, saline water, culture medium (for bacterial analysis), KOH solution (for fungal analysis), etc. Alternatively, such means for preserving or preparing the specimen can be added into the recipient after it arrives at the testing and diagnostic facility, such as a laboratory. Preferably, said means for preserving or preparing the specimen can occupy half or less of the volume of the sealable recipient. When the user introduces the collecting device pouch-first into the recipient, the pouch will occupy a small volume at the bottom of the recipient. The recipients are normally kept in the testing facility in a stand-up position, such as in a tube stand. Consequently, due to the small volume of the creased pouch and to its position at the bottom of the recipient, the entire pouch can be submerged into a smaller volume of said means for preserving or preparing, ensuring that the greatest possible amount of specimens are preserved and recovered from the entire surface of the pouch without having to use a big volume of said preserving or preparing means.

Process for Manufacturing

In another aspect of the present invention, it is disclosed a process for manufacturing a collecting device according to a preferred embodiment of the invention.

The collecting devices of the present invention may be produced by any method suitable for processing one or more suitable sheet(s) of fabric together with creasing means into the collecting device as disclosed above.

In particular, it is disclosed a process for manufacturing a collecting device according to a preferred embodiment of the invention, the process comprising:
a) continuously feeding to a fastening and cutting machine, from separate coils, two similar sheets of fabric and two creasing means, for example two threads, such that they assemble on a manufacturing line in a sandwich-like assembly with the two sheets of fabric covering each other and the creasing means running along between said two sheets of fabric;
b) applying fastening means to said sandwich-like assembly, for example welding means, such as ultrasound welding, thus fastening said two sheets of fabric together by fastening elements such as rows of welding spots and/or lines of continuous welding to form the pouch of the collecting device while at the same time the fastening elements forming the short side of the pouch also fix the two creasing means inside the pouch, and simultaneously
c) applying cutting means to cut the two sheets of fabric and the two creasing means to obtain the desired final shape of the collecting device.

By setting the machine to apply said fastening and cutting means simultaneously and repeatedly (for example by using a rotary mold) to said sandwich-like structure continuously running on the manufacturing line, collecting devices are produced continuously in a single passing of the raw materials through the machine, in a process that is efficient, fast and with minimum waste of materials. The collecting device thus produced can have the mentioned two flaps at the proximal end, for a more efficient sampling, and/or the mentioned further segments narrowing down toward the distal end of the device, for a more comfortable fit and for ease of using the creasing means. Also, the mentioned creasing means are cut together with the distal end of the sheets, such that their distal ends are at the same distance from the proximal end of the device as the distal margins of said further segments, so that they do not protrude to be used as removal means but can be easily gripped and pulled for creasing the pouch.

Method for Sampling

In another aspect of the present invention, it is disclosed a method for sampling at least one specimen from bodily cavities of humans or animals comprising the steps:
inserting at least part of the collecting device of the invention into a bodily cavity of a human or animal,
removing the collecting device from the bodily cavity,
pulling said two creasing means by their distal extremities, at the same time, in opposite directions, away from each other and substantially perpendicular to the long sides of the pouch, thereby creasing the pouch into a creased shape,
placing the collecting device with the pouch in creased shape inside a sealable recipient
sealing the recipient,
sending the sealed recipient to a testing facility, such as a laboratory, for testing and diagnostic.

Depending on the specific circumstances (such as the humidity inside the user's bodily cavity, the targeted specimen, etc.), the collecting device of the invention may be left inserted into the bodily cavity for a period of time. In a preferred embodiment, for collecting HPV DNA from the human vagina, the collecting device of the invention may be maintained inserted into the vagina for at least 2 minutes, preferably for 2 to 30 minutes, such as 2 to 20 minutes or 2 to 15 minutes.

Preferably, step d) is performed by the user holding the creased pouch by the creasing means and introducing the collecting device into the sealable recipient pouch-first. The small dimensions and rigidity of the creased pouch will allow for an easy insertion, such that no further contact of the pouch with the hand is necessary, thus avoiding the contamination of the sample and/or of the hands. Also, the entire pouch, and especially its proximal end, such as the proximal flaps, will be placed at the bottom of the sealable recipient, ensuring that the area with the greatest probability of having sampled specimens is inserted into the preserving or preparing liquid, even when said liquid is in a smaller volume.

Method for Diagnostic

In another aspect, it is disclosed a method for diagnostic of STIs (Sexually Transmitted Diseases) comprising the steps of:
self-sampling at least one specimen from bodily cavities of humans and animals according to the method of sampling described above,
determining the presence of a STI by analyzing and identifying said at least one specimen from the collecting device.

BRIEF DESCRIPTION OF THE DRAWINGS

FIGS. 2a to 2e represent views of the steps for creasing and placing a collecting device according to an embodiment of the invention within recipient, and sealing said recipient.

EXAMPLES

Figure 4:
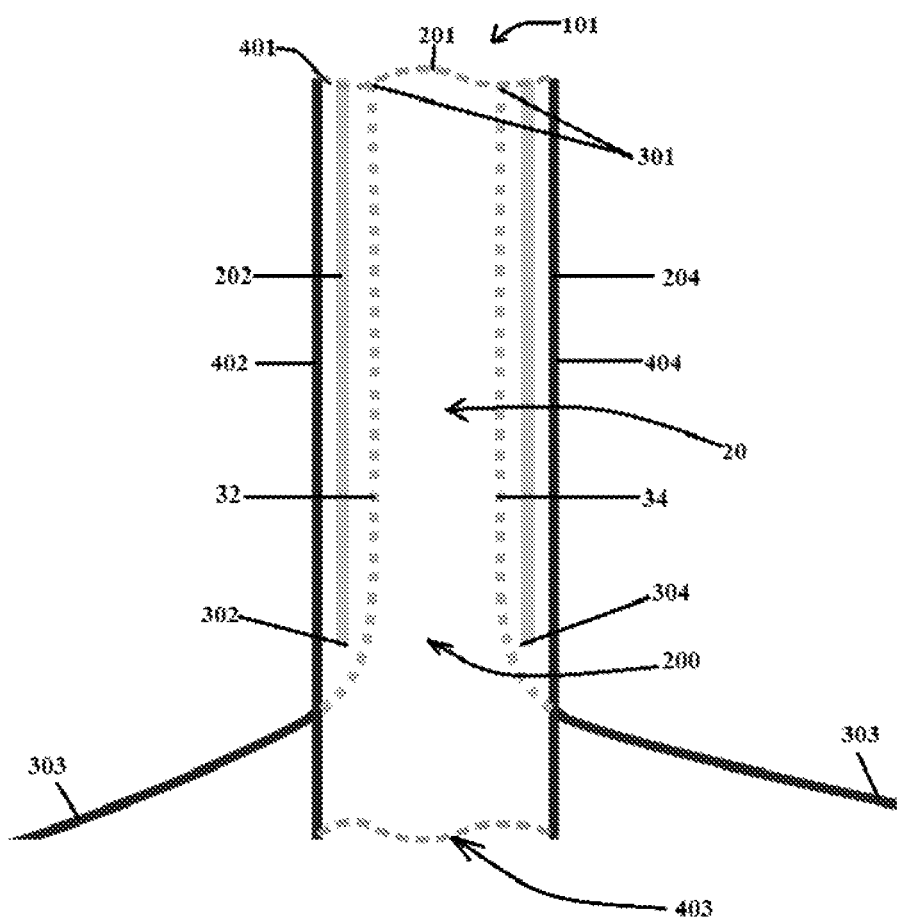
FIG. 4 represents a view of one embodiment of the collecting device without flaps and without further segments.

The collecting device (1) according to one embodiment of the invention is depicted in FIG. 4. The collecting device (1) may comprise, for example, one sheet of fabric bended along the short side (201) of the pouch (20), or two sheets of fabric (40, 41), positioned such that they cover each other at least partially. In FIG. 4 it is shown a front view of an embodiment wherein two sheets of fabric (40, 41) having substantially rectangular similar shapes are placed to cover each other, such that only one of the sheets (40,41) is visible in this front view. Said sheets of fabric (40,41) each have a proximal margin (401) that forms the proximal end (101) of the collecting device (1), two lateral margins (402,404) and a distal margin (403) opposite said proximal margin (401). The two sheets (40,41) are fastened to each other by fastening elements (25), to form an elongated flattened pouch (20). In the present embodiment, the fastening means (25) are placed at the proximal margin (401) to form the short side (201) of the pouch (20) and in the vicinity lateral margins (402,404) to form the long sides (202,204) of the pouch (20).

The two creasing means (32,34) are represented in FIG. 4 by dotted lines where they are inside the pouch (20), and by regular lines where they protrude from the pouch (20) through the open end (200) of the pouch (20). Each of the two creasing means has a fixed end (301), which is fixed inside the pouch (20) at or in the vicinity of the short side (201), and a free end (303), which protrudes freely through said open end (200). In the present embodiment, the creasing means (32,34) are longer than the two sheets of fabric (40,41), so they can be used also as means for removal of the collecting device (1) from the bodily cavity. The creasing means (32,34) can be pulled by said free ends (303) in opposite directions each substantially perpendicular to one of the two long sides (202,204), thus sliding along bending points (302, 304) at the distal extremities of the long sides (202, 204) and bringing the short side (201) of the pouch closer to the open end (200).

Figure 1A:
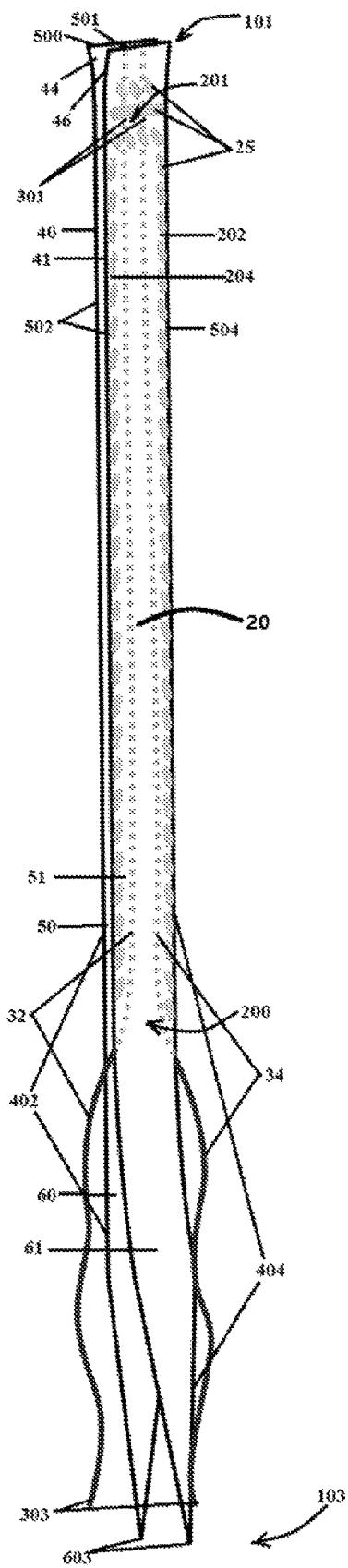
FIG. 1a represents a semi-frontal view of a preferred embodiment according to the invention wherein the collecting device is made of two sheets of fabric and has proximal flaps and further sections that narrow down into a V-shape

FIG. 1a depicts a preferred embodiment of the collecting device (1) of the present invention, wherein the collecting device (1) comprises two sheets of fabric (40, 41), each comprising a first segment (50,51) that enters the bodily cavity when in use. In this embodiment, the two first segments (50,51) have substantially rectangular similar shapes, with the long sides of the rectangles forming lateral margins (502,504), and one of the short sides of the rectangle forming proximal margins (500,501) that are placed at the proximal end (101) of the collecting device (1), the two first segments (50,51) being positioned such that they cover each other, and are fastened to each other by fastening elements (25), to form an elongated flattened pouch (20). The fastening elements (25) form the contour of three sides of a rectangle, bordering a rectangular elongated flattened pouch (20) having an open end (200) that continues with further segments (60,61), a short side (201) opposed to the open end (200), situated at a distance of about 1 mm to 10 mm from said proximal margins (500,501), and two long sides (202,204) placed along the lateral margins (502,504) and running along the length of the lateral margins (502,504) up to the open end (200). By the fact that the short side (201) of the pouch (20) is situated at a distance of about 1 mm to 10 mm from said proximal margins (500,501), the two sheets of fabric (40, 41) form at the proximal end (101) two symmetrical proximal flaps (44, 46). Said flaps (44,46) are attached to each other by the fastening elements (25) along the short side (201) and have each a free margin opposite the short side of the pouch that is also the margin (500, 501) of the respective sheet of fabric (40,41). The two proximal flaps (44,46) are depicted in a closed state, wherein their two free margins (500,501) are very close to each other.

Each of the sheets (40,41) comprises a further segment (60,61) which remains at least partially outside the bodily cavity during use, for gripping and removing the collecting device (1) from the bodily cavity, said further segments (60,61) not being fastened to each other. Both further segments (60,61) have a distal termination (603) with a V-shape that narrows toward the distal end (103) of the collecting device (1).

The two creasing means (32,34) are represented in FIG. 1a by dotted lines where they are inside the pouch (20), and by regular lines where they protrude from the pouch (20). Each of the two creasing means has a fixed end (301), which is fixed inside the pouch (20) at the short side (201), and a free end (303), which protrudes freely through said open end (200), and reaches to about the same length as the distal termination (603) of said further segments (60, 61).

Figure 1B:
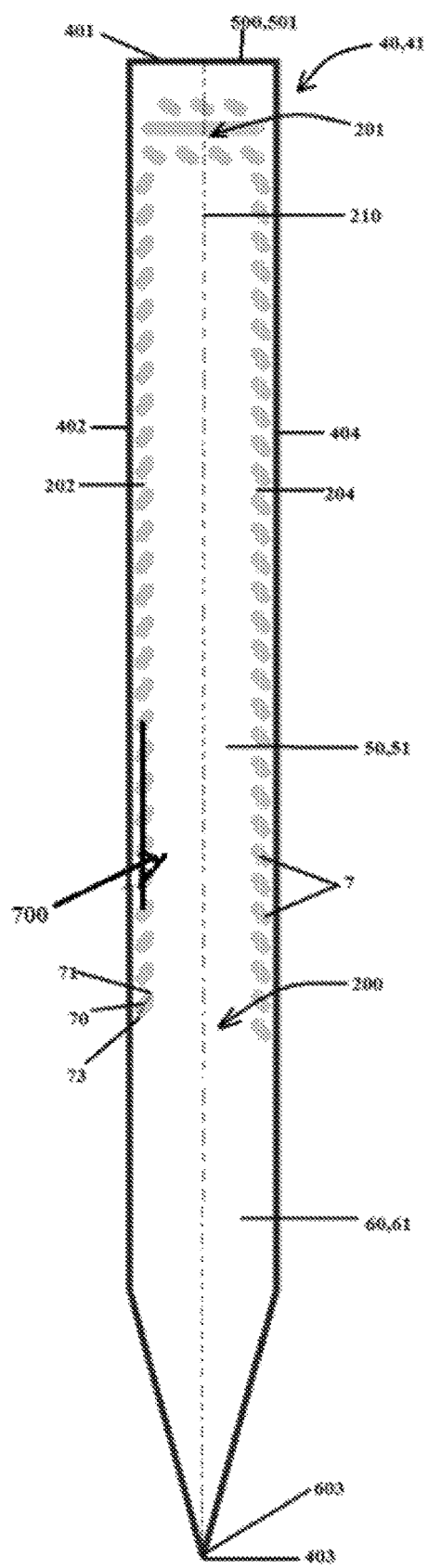
FIG. 1b represents a frontal view of the preferred embodiment in FIG. 1, wherein the fastening elements along the long sides of the pouch are made of rows of welding spots placed at an angle to the long sides.

FIG. 1b depicts a front view of the collecting device (1) of FIG. 1a, wherein only one of the sheets of fabric (40,41) is visible, and none of the creasing elements (32,34). In this embodiment, the fastening elements (25) forming the long sides (202,204) of the pouch (20) are single straight rows of welding spots (7). Each welding spot (7) has a substantially elongated shape with a long axis (70), a proximal end (71) and a distal end (73). In the present, preferred embodiment, the elongated welding spots (7) are placed in the corresponding rows such that the long axes (70) of each welding spot forms a similar angle (700) to the direction of their corresponding row. The angle (700) is an acute angle formed by the long axes (70) of the welding spots to the direction of the corresponding long side (202,204) toward the proximal end (101) of the collecting device (1). Therefore, the proximal end (71) of each welding spot (7) is at the same time closer to the short side (201) of the pouch and to a longitudinal central axis (210) of the pouch (20). This arrangement has the effect that, when pulling on the creasing means (32,34), the angled welding spots (7) lead the pouch to fold into small, even, regular, symmetric creases, thus adopting a compact creased shape that is easier to introduce into a recipient.

Moreover, in the present preferred embodiment, the fastening elements (25) forming the short side (201) of the pouch (20) are made of two rows of welding spots (7) and a line of continuous welding placed between the two rows. Such fastening element (25) is more resistant to the force exerted by the applicator (8) and also ensures that each of the creasing means (32,34) is fixed in at least one point.

Figure 1C:
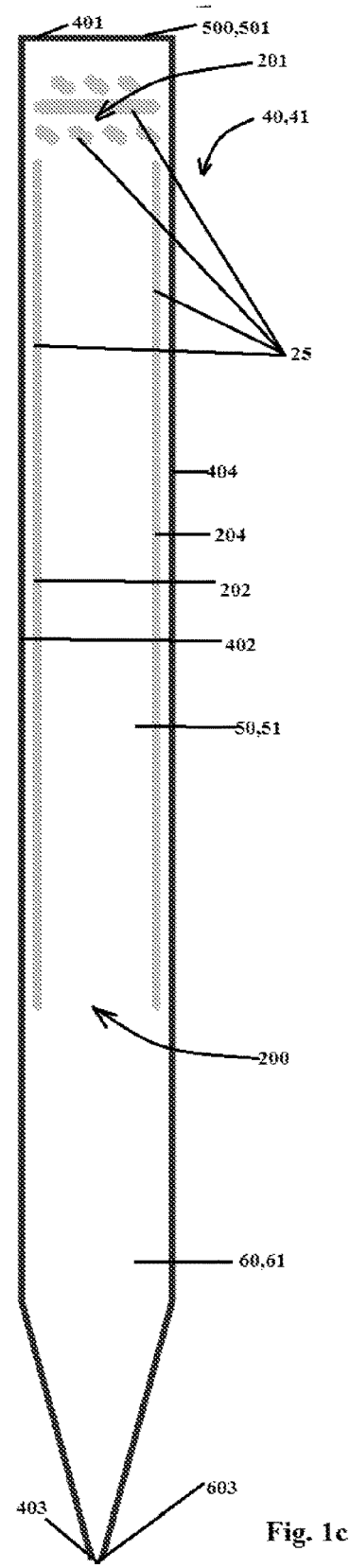
FIG. 1c represents a frontal view of an embodiment wherein the fastening elements along the long sides of the pouch are made of continuous welding lines.

FIG. 1c depicts a front view of an embodiment wherein only one of the sheets of fabric (40,41) is visible, and none of the creasing elements (32,34). In this embodiment, the fastening elements (25) forming the long sides (202,204) of the pouch (20) are single straight rows of continuous welding.

FIGS. 2a-2e represents views of the steps for creasing and placing a collecting device (1) according to an embodiment of the invention within a sealable recipient (9), and sealing said recipient (9).

FIG. 2a shows how the collecting device (1) that has been removed from the bodily cavity is gripped by the free ends (303) of the creasing means (32,34).

FIGS. 2b and 2c show how, by pulling on said free ends (303) of the creasing means (32,34) in opposite directions each substantially perpendicular to one of the two long sides (202,204), the short side (201) of the pouch is brought closer to the open end (200) while the pouch (20) adopts an increasingly contracted shape until it reaches a creased shape (22) shown in FIG. 2c.

FIG. 2d shows how the collecting device (1) having the pouch (2) in creased shape (22) is held by the creasing means (32,34) and introduced into the sealable recipient (9), which is a testing tube with a thread cap. The small dimensions and rigidity of the pouch (20) in creased shape (22) allow for an easy insertion, such that no further contact of the pouch with the hand is necessary, thus avoiding the contamination of the sample and/or of the hands.

FIG. 2e shows the recipient (9) after the collecting device (1) has been inserted and the thread cap has been closed, thus sealing the recipient (9).

FIGS. 3a to 3e represent sequential views of some steps of a method for sampling according to the invention, with an embodiment wherein the collecting device (1) is provided with proximal flaps (44,46) and is inserted inside a vaginal cavity.

Figure 3A:
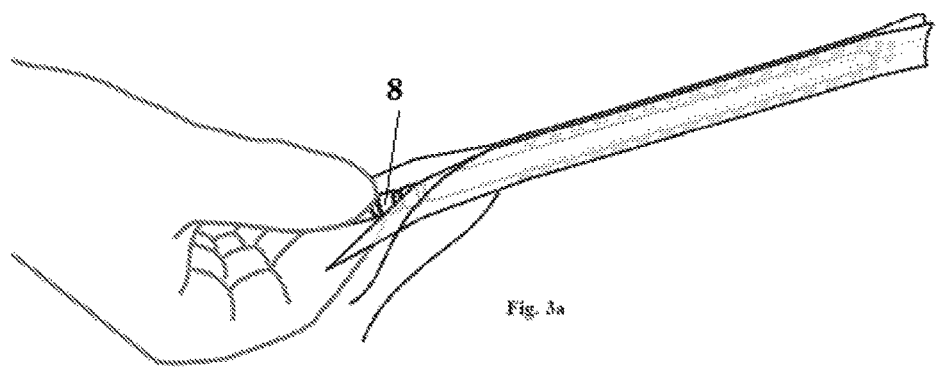
FIGS. 3a to 3e represent sequential views of some steps of the method for sampling according to the invention, with an embodiment wherein the collecting device is provided with proximal flaps.

FIG. 3a shows a collecting device (1) as depicted in FIG. 1 with the applicator (8) introduced into the pouch (20), ready for insertion inside the vaginal cavity (30). It can be seen that most of the length of the applicator (8) is covered by the collecting device (1), so the vaginal mucosa is protected from direct contact with the applicator (8).

Figure 3B:
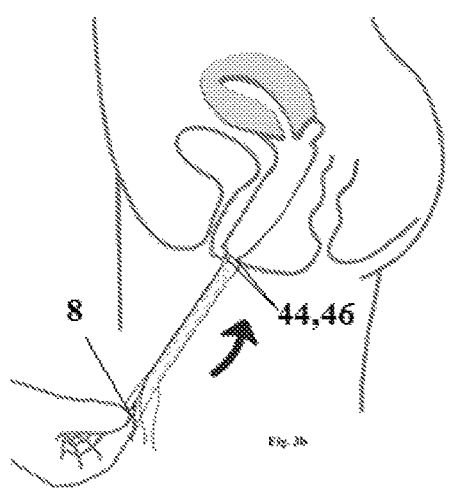

FIG. 3b shows the collecting device (1) as it is positioned at the entrance of the vaginal cavity for insertion. It can be seen that the two symmetrical proximal flaps (44,46) of the collecting device are in closed state, wherein their two free margins (500,501) touch or are very close to each other.

Figure 3C:
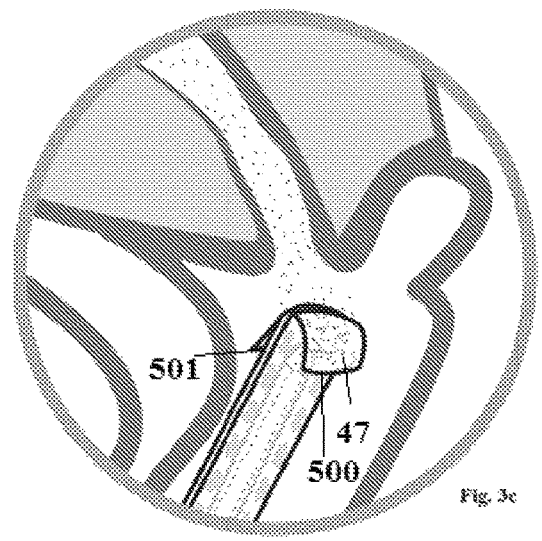

FIG. 3c shows the proximal end (101) of collecting device (1) after insertion into the vaginal cavity. It can be seen that the two flaps (44,46) have transitioned during insertion an open state, wherein their two free margins (500,501) get away from each other and their inner faces (47) are positioned to receive specimens from the endocervical canal and cervical os.

Figure 3D:
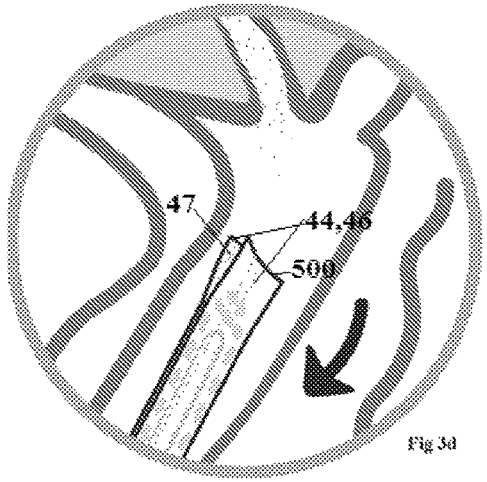

FIG. 3d shows the proximal end (101) of collecting device (1) during removal from the vaginal cavity. It can be seen that, due to the direction of removal, the proximal flaps (44,46) transition back to the closed state, thus catching the specimens on their inner faces (47) between the flaps (44,46). This ensures that a sufficient amount of specimens are successfully sampled and kept on the inner faces (47) of the flaps (44,46), which are not lost due to the friction of the collecting device (1) with the walls of the vaginal cavity during removal.

Figure 3E:
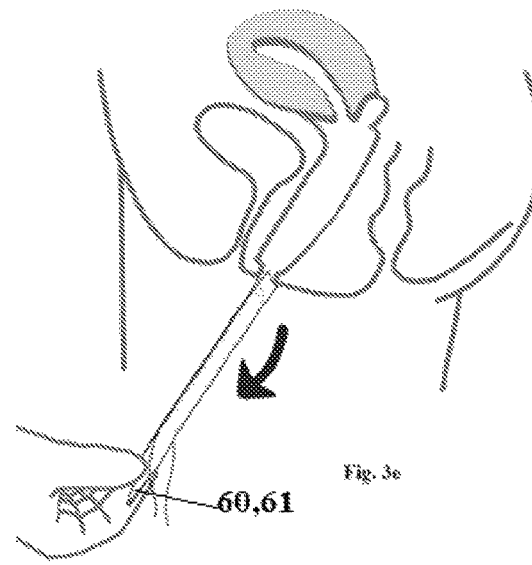

FIG. 3e shows the collecting device (1) after removal from the vaginal cavity. It can be seen that the collecting device has been removed by using the further segments (60,61) as removal means. It is also vicible that the flaps (44,46) have remained in closed state during removal.

The invention claimed is:

1. Collecting device for sampling at least one specimen from bodily cavities of humans and animals,
   the collecting device having a proximal end, which is the end of the device to first contact said bodily cavity during use and a distal end opposed to said proximal end,
   the collecting device comprising:
   an elongated ouch made of fabric, the pouch configured to maintain a square- ended, flat shape while the pouch is sampling the at least one specimen from said bodily cavity, the pouch having:
   an a single open end, a primary side opposed to the open end, situated at the proximal end of the collecting device, and two secondary sides;
   wherein the collecting device further comprises two creasing means, each having a fixed end, each fixed end being fixed to an inside surface of the pouch opposite the open end,
   and a free end which protrudes freely through said open end,
   wherein the collecting device is configured such that upon pulling the free ends of the two creasing means in opposite directions each transverse to one of the two secondary sides,
   the primary side of the pouch is brought closer to the open end while the pouch adopts a creased shape;
   wherein the primary side is shorter than the secondary sides.

2. Collecting device according to claim 1
   wherein the pouch is made of a flexible fabric suitable for collecting at least one specimen such as a cell, cell residue, DNA, RNA, protein, virus, bacterium, parasite, or fungus, such as a fabric with an absorbency of 3.5 g/g or less.

3. Collecting device according to claim 2,
   wherein the device further comprises at least one further segment integrally formed with the fabric of the pouch,
   said further segment extending from the open end of the pouch towards the distal end of the collecting device,
   and said further segment having dimensions such that, after the collecting device is inserted into the bodily cavity, said at least one further segment protrudes outside said bodily cavity.

4. Collecting device according to claim 1,
   wherein each of said creasing means is in the form of a thread, elastic thread, string, strip or ribbon.

5. Collecting device according to claim 1,
   wherein the collecting device comprises two sheets of fabric, each having a proximal margin situated at the proximal end of the device, a distal margin situated at the distal end of the device, and two lateral margins,
   wherein the sheets are fastened to each other by fastening elements to form the primary side and the two secondary sides of the pouch.

6. Collecting device according to claim 5, wherein said two secondary sides of the pouch are parallel to each other and perpendicular to said primary side.

7. Collecting device according to claim 5, wherein said primary side of the pouch is situated at a distance of 1 mm to 10 mm from the proximal margin of said sheets.

8. Collecting device according to claim 7
   wherein said primary side of the pouch forms two proximal flaps fixed to each other at one end by the fastening elements at the primary side and having the opposite end free.

9. Collecting device according to claim 5,
   wherein said secondary sides of the pouch are situated at or in the vicinity of the lateral margins of the sheets.

10. Collecting device according to claim 5,
    wherein the fastening elements at the primary side of the pouch are made of two or more rows of welding spots and/or lines of continuous welding.

11. Collecting device according to claim 5,
    wherein each sheet of fabric has a segment that is fastened to the other sheet to form the pouch and at least one of said sheets of fabric has further segment, at the distal margin, that is not fastened.

12. Collecting device according to claim 11,
    wherein at least one of said further segments has a V-shape that narrows toward the distal end of the collecting device.

13. Collecting device according to claim 11,
    wherein the fee end of each of said creasing means can reach out of the pouch to a point that is at least 10 mm beyond said open end of the pouch, but not beyond a distal termination of the further segments.

14. Collecting device according to claim 5,
    wherein said fastening elements forming the two secondary sides of the pouch are single straight rows of welding spots having elongated shapes, each welding spot defining a long axis, a proximal end and a distal end, oriented so that said long axis of each welding spot forms an angle to the corresponding secondary side that the welding spot is part of, such that the proximal end that is closer to the primary side of the pouch is also the end of the welding spot that is closer to a longitudinal central axis of the pouch, thus the long axis of the welding spot forming an acute angle to the direction toward the proximal end of the corresponding secondary side.

15. Sampling kit, comprising a collecting device according to claim 1, an applicator for inserting into the pouch to introduce at least part of said collecting device inside a bodily cavity, and a sealable recipient for receiving the device after sampling.

16. Method for sampling at least one specimen from bodily cavities of humans or animals by using a collecting device according to claim 1, wherein the bodily cavities may be either one of vaginal cavity, rectal cavity, or nasal cavity.

17. Method for sampling at least one specimen from bodily cavities of humans or animals according to claim 16, the method further comprising the steps:

a) inserting at least part of the collecting device into a bodily cavity of a human or animal, b) removing the collecting device from the bodily cavity, c) pulling said two creasing means by their distal extremities, at the same time, in opposite directions, away from each other and transverse to the secondary sides of the pouch, thereby creasing the pouch into a creased shape, d) placing the collecting device with the pouch in creased shape inside a sealable recipient e) sealing the recipient, f) sending the sealed recipient to a testing facility for testing and/or diagnostic.

18. Method for sampling according to claim 17, wherein after step a) and before step b), the pouch is left inserted into the bodily cavity for a period of time of at least 2 minutes.

19. A process for manufacturing a collecting device according to claim 5, the process comprising:

a) continuously feeding to a fastening and cutting machine, from separate coils, two similar sheets of fabric and two creasing means, for example two threads, such that they assemble on a manufacturing line in an assembly with the two sheets of fabric covering each other and the two creasing means running along between said two sheets of fabric;

b) applying fastening means to said assembly, thus fastening said two sheets of fabric together by fastening elements to form the pouch of the collecting device while at the same time the fastening elements forming the primary side of the pouch also fix the two creasing means inside the pouch, and simultaneously c) applying cutting means to cut at the same time the two sheets of fabric and the two creasing means to obtain the desired final shape of the collecting device.

* * * * *